United States Defensive Publication [19] (H) [11] T102,908

Halpern et al. [43] Apr. 5, 1983

[54] CATALYZED TRANSESTERIFICATION SYNTHESIS

[76] Inventors: Joseph Halpern, 1072 Springfield Ave., New Providence, N.J. 07974; Phillip Adams, 27 Burlington Rd., Murray Hill, N.J.

[21] Appl. No.: 382,007

[22] Filed: May 25, 1982

Related U.S. Application Data

[63] Continuation of Ser. No. 801,345, May 27, 1977, abandoned.

[51] Int. Cl.[3] ..... C07C 69/74

[52] U.S. Cl. ..... 560/124

[57] ABSTRACT

Esters of the formula

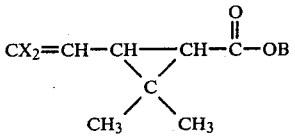

wherein X is chlorine or bromine and B is a benzyl group of the formula

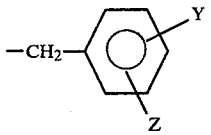

where Y and Z may be the same or different and are selected from the group consisting of hydrogen, halogen, lower alkyl, lowr alkoxy, phenyl, phenoxy, lower alkyl phenyl, lower alkyl phenoxy, halophenyl and halophenoxy, are prepared by transesterification between BOH and a compound of the formula

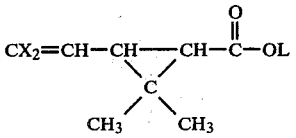

wherein L is a lower alkyl radical of between 1 and 4 carbon atoms, using as catalyst an organometallic compound selected from $(RO)_4Ti$ and $R'_2SnO$, where R and R′ are alkyl radicals of between 1 and 6 carbon atoms.

Useful organometallic catalysts include tetrabutyl titanate, tetraisopropyl titanate, and dibutyl tin(IV)oxide. About 1% by weight of the total charge of reactants is catalyst.

The process is conducted at 100°–200° C. under vacuum, generally in the absence of solvent, with sustained distillation of the LOH by-product until the theoretical amount of alcohol is collected. The product ester is then distilled under vacuum.

For example, 126 g ethyl 3-(2,2-dichlorovinyl)-2,2-dimethylcyclopropanecarboxylate, 100 g m-phenoxybenzyl alcohol, and 2.25 grams of tetraisopropyl titanate reacted at 150° C./200 mm Hg yielded the m-phenoxybenzyl ester; bp 181° C./0.1 mm Hg, 89% yield, 99.5% pure.

1 Claim, No Sheets Drawing,

12 Pages Specification

The file of this unexamined application may be inspected and copies thereof may be purchased (849 O.G. 1221, Apr. 9, 1968).